US011679380B2

(12) United States Patent
Yoo et al.

(10) Patent No.: US 11,679,380 B2
(45) Date of Patent: Jun. 20, 2023

(54) DOUBLE-LAYER-STRUCTURED CATALYST FOR DEHYDROGENATING LIGHT HYDROCARBONS

(71) Applicant: HEESUNG CATALYSTS CORPORATION, Gyeonggi-do (KR)

(72) Inventors: Young-san Yoo, Gyeonggi-do (KR); Hyun A Choi, Incheon (KR); Dong Kun Kang, Gyeonggi-do (KR); Young Ho Lee, Gyeonggi-do (KR)

(73) Assignee: HEESUNG CATALYSTS CORPORATION, Gyeonggi-Do (KR)

( * ) Notice: Subject to any disclaimer, the term of this patent is extended or adjusted under 35 U.S.C. 154(b) by 284 days.

(21) Appl. No.: 17/057,216

(22) PCT Filed: May 17, 2019

(86) PCT No.: PCT/KR2019/005911
§ 371 (c)(1),
(2) Date: Nov. 20, 2020

(87) PCT Pub. No.: WO2019/225906
PCT Pub. Date: Nov. 28, 2019

(65) Prior Publication Data
US 2021/0205802 A1    Jul. 8, 2021

(30) Foreign Application Priority Data

May 21, 2018  (KR) .................. 10-2018-0057572

(51) Int. Cl.
| | | |
|---|---|---|
| *B01J 35/00* | (2006.01) | |
| *B01J 23/58* | (2006.01) | |
| *B01J 23/62* | (2006.01) | |
| *B01J 35/02* | (2006.01) | |
| *C07C 5/32* | (2006.01) | |

(52) U.S. Cl.
CPC ........... *B01J 35/0073* (2013.01); *B01J 23/58* (2013.01); *B01J 23/626* (2013.01); *B01J 35/02* (2013.01); *C07C 5/325* (2013.01)

(58) Field of Classification Search
CPC ........ B01J 35/0073; B01J 35/02; B01J 23/58; B01J 23/626; C07C 5/325
See application file for complete search history.

(56) References Cited

U.S. PATENT DOCUMENTS

| | | | | |
|---|---|---|---|---|
| 4,716,143 A | | 12/1987 | Imai .............................. | 502/326 |
| 4,786,625 A | * | 11/1988 | Imai ....................... | C10G 45/00 |
| | | | | 502/514 |
| 6,280,608 B1 | * | 8/2001 | Jensen ................. | B01J 37/0219 |
| | | | | 208/143 |
| 2018/0311644 A1 | | 11/2018 | Han et al. | |
| 2018/0311645 A1 | | 11/2018 | Han et al. | |

FOREIGN PATENT DOCUMENTS

| | | |
|---|---|---|
| JP | 07-004529 | 1/1995 |
| KR | 10-1989-0000516 | 3/1989 |
| KR | 10-1716170 | 3/2017 |
| KR | 10-2017-0054789 | 5/2017 |
| WO | PCT/KR2019/005911 | 5/2019 |
| WO | WO 2019/225906 | 11/2019 |

OTHER PUBLICATIONS

International Search Report and Written Opinion dated Sep. 5, 2019 by the International Searching Authority for International Application No. PCT/KR2019/005911, filed May 17, 2019 and published as WO 2019/225906 on Nov. 28, 2019 (Applicant—Heesung Catalysts Corporation) (8 Pages).

* cited by examiner

*Primary Examiner* — Yong L Chu
(74) *Attorney, Agent, or Firm* — Ballard Spahr LLP

(57) ABSTRACT

A double-layer structured catalyst for use in dehydrogenation of light hydrocarbon gas within a range of C3 to C6, configured such that platinum, tin, and an alkali metal are carried in a phase-changed carrier, wherein the tin component is present in an entire region inside the carrier, and the platinum and the tin form a single complex and are present in an alloy form within a range of a predetermined thickness from an outer periphery of the carrier.

2 Claims, 2 Drawing Sheets

[FIG. 1]
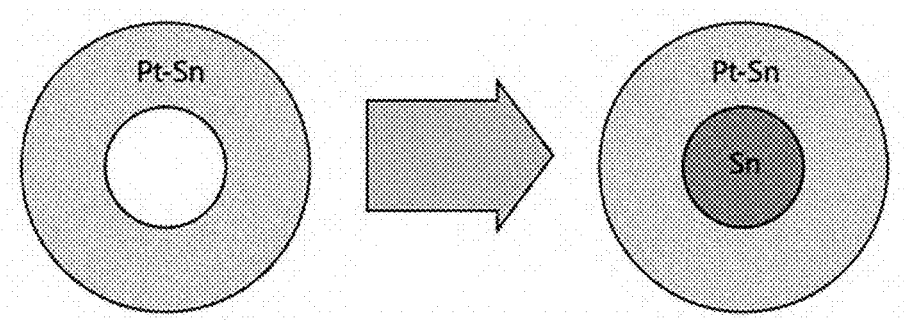
[FIG. 2]
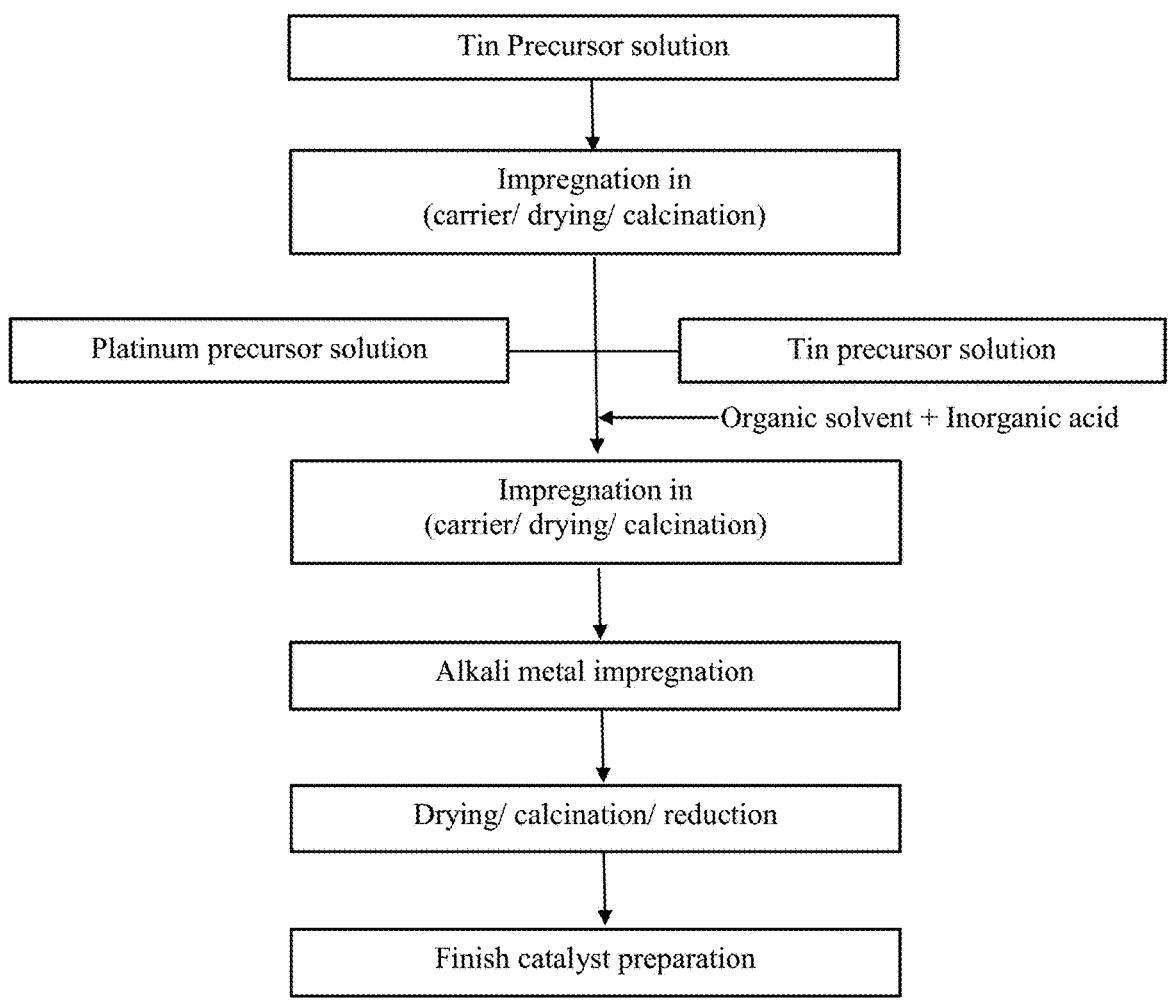

[FIG. 3]
(a)
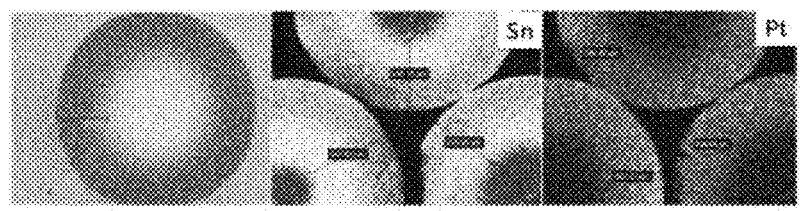
(b)
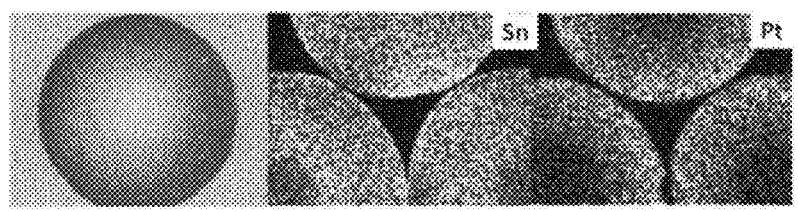
[FIG. 4]
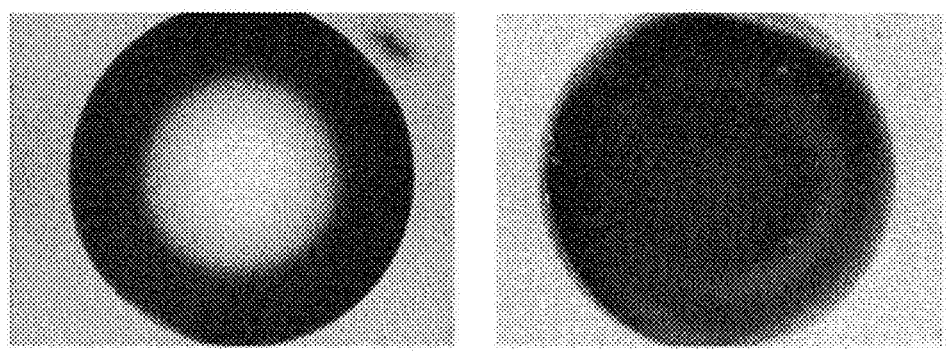

DOUBLE-LAYER-STRUCTURED CATALYST FOR DEHYDROGENATING LIGHT HYDROCARBONS

CROSS-REFERENCE TO RELATED APPLICATIONS

This application is a U.S. National Phase Application of International Application No. PCT/KR2019/005911, filed May 17, 2019, which claims priority to Korean Application No. 10-2018-0057572, filed May 21, 2018, each of which are hereby incorporated by reference in their entirety.

TECHNICAL FIELD

The present disclosure relates to a double-layer structured catalyst for dehydrogenating light hydrocarbons and a method of manufacturing the same. More particularly, the present disclosure relates to a technology of a catalyst and a manufacturing method of the catalyst, in which the catalyst contains two kinds of metal components in an alloy form present within a range of a predetermined thickness on a surface of a catalyst carrier and one of the two kinds of metal components is distributed in an entire region of the catalyst, and the catalyst has high durability and high regeneration efficiency when used in dehydrogenation of light hydrocarbons.

BACKGROUND ART

A dehydrogenation of light hydrocarbons using a catalyst has advantages in that a product having a high yield and a high purity is obtained, and is a reaction having a high manufacturing efficiency and simple process. Therefore, research related to the manufacture of light olefins by dehydrogenation using a catalyst has been ongoing steadily.

The present applicant has disclosed a catalyst that exhibits improved selectivity and reactivity, and is suitable for use in the manufacture of an olefin by dehydrogenating C3, C4, or C9 to C13 paraffin. More particularly, a technology for manufacturing a catalyst configured such that a thermally treated carrier having controlled pores is used and most metal components contained in the catalyst are uniformly distributed not in the form of individual metals but in the form of an alloy in the carrier from the outer periphery or in the entire region of the catalyst (Korean Patent Application Publication No. 10-2017-0054789, Published on May 18, 2017 and Korean Patent No. 10-176170, Published on Mar. 14, 2017). In the related art of a dehydrogenation catalyst, for active site control, since dehydrogenation intensity of platinum is too strong, an alkali metal is introduced, and tin is introduced in an effort to prevent deterioration of catalyst activity due to carbon deposition.

DISCLOSURE

Technical Problem

According to the related art, there is a problem in that since a catalyst in which platinum and tin in the form of an alloy are distributed partially within an outer surface portion or uniformly within an entire region of an alumina carrier is used, the catalyst activity is lowered due to a situation that a carbon coke deposited in the alumina carrier covers an active site, and even when the coke is removed from the carrier by using a calcination process, it is almost impossible to completely regenerate the catalyst into an initial state due to the coke which remains therein.

Technical Solution

In order to achieve the above objectives, according to one aspect of the present disclosure, there is provided a double-layer structured catalyst for use in dehydrogenation of light hydrocarbon gas within a range of C3 to C6, configured such that platinum, tin, and an alkali metal which are carried in a phase-changed carrier, and the tin component is present in an entire region inside the carrier, and the platinum and the tin form a single complex and are present within a range of a predetermined thickness from an outer periphery of the carrier.

In another embodiment of the present disclosure, the single complex of platinum and tin is formed within a range of a thickness of 300 to 500 μm from the outer periphery of the carrier, and the carrier may be selected from the group consisting of alumina, silica, zeolite, and a complex component thereof.

In the present disclosure, a catalyst for dehydrogenating a light paraffinic hydrocarbon has actually the same aspect as that of the related art in that an alloy of platinum and tin in the carrier are present within a range of a predetermined thickness from the surface of the carrier to the inner core. However, it should be noted that unlike the related art, the tin component in the catalyst of the present disclosure is uniformly distributed in the inner core. This new double-layer structure induces a coke to be formed extensively inside the carrier rather than only the dehydrogenation active site, and thus increases durability and also minimizes aging due to a coke oxidation so that a catalyst that inhibits the sintering of active metals may be provided.

An objective of the present disclosure is to improve efficiency of activation and regeneration by the influence of the coke by placing coke-inducing material in the center of the carrier in contrast to the related art which does not have an active metal in the inner core of the carrier.

Advantageous Effects

In the catalyst having the double-layer structure according to the present disclosure, the tin component is uniformly present in the core of the carrier, while the platinum and the tin in the form of an alloy are distributed within a range of a predetermined thickness inside the carrier. Here, the tin component distributed to the center or to the core of the carrier spreads the coke generation not only onto the active site of the alloy of platinum and tin but also into the inside of the carrier, thus minimizing the inactive phenomenon of the platinum caused by the coke generation, and increasing the durability of the catalyst, while reducing the formation of the coke on the active site, so that the aging of the catalyst is reduced and the sintering of the platinum is prevented, whereby the improved regeneration of the catalyst is realized.

DESCRIPTION OF DRAWINGS

FIG. 1 is a view schematically illustrating a structural difference of a catalyst that has been improved from a conventional technology to a double-layer structured catalyst of the present disclosure;

FIG. 2 is a flowchart illustrating a manufacturing process of the double-layer catalyst of the present disclosure;

FIG. 3 illustrates electron probe microanalysis (EPMA) images comparing a catalyst of the conventional technology (a) with a double-layer structured catalyst of the present disclosure (b);

FIG. 4 illustrates electron microscope images (video microscopy) comparing a state of a catalyst of the conventional technology with the double-layer structured catalyst of the present disclosure before regeneration.

BEST MODE

The present disclosure relates to a double-layer structured catalyst for dehydrogenating light hydrocarbons and a method of manufacturing the same. More particularly, the present disclosure relates to a catalyst and manufacturing of method of the catalyst, in which the catalyst contains two kinds of metal components, for example, platinum and tin in an alloy form are present within a range of a predetermined thickness on a surface of the carrier, and one of the two kinds of metal components, for example, the tin is distributed within an entire region of the catalyst, whereby the catalyst is improved in durability and regeneration efficiency when used in dehydrogenation of light hydrocarbons since the coke generation is distributed to the entire region of the carrier.

From the conventional technology, it has been noted that when the active metals of the dehydrogenation catalyst of light paraffinic hydrocarbons are not distributed alone in the carrier but the active metals in an alloy form are present within a range of a predetermined thickness from the surface of the catalyst to the inside thereof, it is possible to manufacture a catalyst capable of greatly increasing the conversion rate of paraffin, olefin selectivity, and durability. However, problems still remain due to coke.

In the present disclosure, the active metal of the catalyst refers to platinum, but comprehensively includes tin, and the double-layer refers to a structure wherein the inside of the carrier is divided into two layers. For example, the alloy of the platinum and tin is present in the outer layer, and the tin component is placed in the inner layer. The term 'double-layer' contrasts with a structure of the conventional technology which did not have any active component in the inner core. In the present disclosure, the term 'alloy' may be used interchangeably with the term 'complex'. The inner layer of the carrier may be referred to as the 'core', 'egg', or 'center', and the outer layer of the carrier may be referred to as the 'shell'. An outer layer thickness or a core depth may vary depending on the alloy depth. In other words, the thickness or the depth of the outer and inner layers may vary depending on the alloy depth and is not fixed. In the present disclosure, the carrier may be selected from the group of consisting of alumina, silica, zeolite, and a complex component thereof. In addition, the light hydrocarbon gas refers to light paraffin. More particularly, the light hydrocarbon gas is straight chain-type or branch-type hydrocarbons in a range of C3 to C6. The catalyst for dehydrogenation of light hydrocarbons is subjected to a relatively high-temperature reaction compared to heavy hydrocarbons, thus forming a large amount of coke due to thermal decomposition and other side reactions. However, surprisingly, the problem of the coke was solved by placing the tin component in the core of the dehydrogenation catalyst carrier of the related art. Specifically, the tin component placed up to the center of the carrier spreads coke generation not only to the active sites of alloy of platinum and tin but also to the inside of the carrier, thus improving the durability of the catalyst by minimizing a covering phenomenon of the platinum. Moreover, by minimizing the generation of the coke on the active sites, the sintering phenomenon of the platinum was prevented by reducing aging during the regeneration process, thereby realizing improved regeneration efficiency of the catalyst. In other words, the coke density in the active component alloy is decreased.

In the present disclosure, a process of carrying the tin of uniform distribution on the core of the carrier is performed before carrying an active metal alloy complex, and the platinum and tin are formed into the complex within an organic solvent and are simultaneously carried with a certain amount of inorganic acids and/or a certain amount of organic acids, and distributing them within a range of a predetermined thickness on the surface of the carrier is performed to complete the catalyst manufacture.

FIG. 1 is a view schematically illustrating a structural difference of a catalyst that has been improved from a conventional technology to a double-layer structured catalyst of the present disclosure. In a dehydrogenation catalyst of the conventional technology, platinum and tin form a single complex and are present within a range of a predetermined thickness from the outer periphery of the carrier. For example, platinum and tin are present in the shell as an alloy, whereas the dehydrogenation catalyst of the present disclosure has a shell-egg structure with an evenly added tin component in the core of the carrier.

FIG. 2 is a flowchart illustrating a manufacturing process of the double-layer catalyst of the present disclosure, which comprehensively explains the method of the present disclosure.

1) Pre-Treatment Process with the Tin Precursor Solution

In order to increase the pore size and the pore volume, the carrier is heat-treated in a calcination furnace at 1000 to 1050° C. for 1 to 5 hours, whereby gamma alumina is phase-changed to theta alumina prior to using the carrier. During the manufacture of the tin precursor, a certain amount of the tin precursor is mixed with an excessive amount of inorganic acid such as hydrochloric acid and nitric acid, and placed the mixture in deionized water, where the excessive amount of the inorganic acid acts as a double role that makes the melting of the tin precursors in the deionized water easy and ensures that the tin precursor reaches the core portion of the carrier. The carrier is placed in the produced tin precursor solution until that the carrier is completely submerged, and the carrier is aged for 2 to 24 hours to allow the tin component to reach the core of the carrier, and then a filtering process is performed to remove moisture therefrom primarily. Thereafter, a drying process is performed at 80 to 150° C. for 24 hours, thus secondarily and completely removing moisture remaining in the catalyst, and then a calcination process is performed at 400 to 700° C. in air, thus obtaining a pre-treated catalytic structure in which tin is placed in the entire region thereof.

2) Process of Manufacturing Stabilized Platinum-Tin Composite Solution

The composite solution of platinum and tin readily causes precipitation of platinum in air due to the high reducibility of tin. Therefore, selection of a solvent is very important in the manufacture of the composite solution. First, the precursors of platinum and tin were added to the organic solvent so that the platinum-tin composite was not decomposed when being mixed with each other, and hydrochloric acid was added to manufacture an acidic solution. Then, an organic acid was added to the organic solvent in order to increase the penetration speed into the inside of the carrier. During the manufacture of the platinum-tin composite solution, the solution is kept in an inert gas atmosphere and decomposition by oxygen is suppressed whereby stabilization of the solution is achieved. Here, nitrogen, argon, and helium may be used as the inert gas, and nitrogen gas is preferably used.

3) Process of Manufacturing Double-Layer Structured Catalyst Using Stabilized Platinum-Tin Composite Solution and Alkali Metal In the process of carrying the active metal alloy solution, a platinum-tin composite solution is manufactured in an amount of equivalent to the total pore volume of the carrier, and is impregnated in the carrier using a spray-carrying method. After the impregnation, an aging process is performed for a predetermined period of time in order to control the penetration depth of platinum and tin into alumina by an organic acid. After the aging process, a rapid drying process is performed while fluidizing the catalyst in an atmosphere of 150 to 250° C., thus removing most of the organic solvent remaining in the catalyst. Water remaining in the catalyst is completely removed via a drying process at 100 to 150° C. for 24 hours. The reason for performing rapid drying is to prevent the platinum-tin composite solution from diffusing into the carrier together with an inorganic or organic acid solvent over time when the platinum-tin composite solution is carried in the alumina carrier in which the tin component is already placed. After drying, an organic material is removed under a nitrogen atmosphere at 250 to 400° C., followed by a calcination process in an ambient atmosphere at 400 to 700°.

After calcination, a process for carrying alkali metal is performed in order to suppress the catalyst side reaction. First, potassium is carried in the internal pores of the carrier using the same spray-carrying method as in the process of manufacturing the platinum-tin composite solution, and a drying process at 100 to 150° C. for 24 hours, and a calcination process in an ambient atmosphere at a temperature within a range of 400 to 700° C. are performed. Finally, after the calcination, a reduction process is performed using a hydrogen/nitrogen mixed gas (a range of 4%/96% to 100%/0%) at a temperature within a range of 400 to 600° C., thus obtaining a final catalyst.

The electron probe microanalysis (EPMA) images of the double-layer catalyst manufactured by the method are shown in FIG. 3b. FIG. 3a illustrates an electron probe microanalysis (EPMA) image of a catalyst of the conventional technology, and FIG. 3b illustrates an electron probe microanalysis (EPMA) image of a double-layer structured catalyst of the present disclosure. The core of the carrier of the present disclosure has a uniformly distributed tin component, whereas there is no active metal component in the core of the carrier in the conventional technology.

After packing the double-layer structured catalyst manufactured by the method of the present disclosure to a fixed-bed catalytic reactor, and then generating an olefin by the dehydrogenation reaction, whether a coat forms or not inside the catalyst is observed. FIG. 4 illustrates electron microscope images (video microscopy) comparing a state of a catalyst of the conventional technology with the double-layer catalyst of the present disclosure before regeneration. A coke deposition is observed in the core of the double-layer catalyst of the present disclosure as expected, while the coke formation is suppressed in the catalyst of the conventional technology. Therefore, the coke density at the catalyst active site is significantly lower for the double-layer catalyst of the present disclosure, resulting in a substantial increase in durability and regeneration efficiency of the catalyst of the present disclosure.

The invention claimed is:

1. A double-layer structured catalyst for use in dehydrogenation of light hydrocarbon gas within a range of C3 to C6, the catalyst comprising:
   a platinum/tin alloy, a tin component, and an alkali metal which are carried in a theta-alumina carrier,
   wherein the tin component is present in an entire region inside the carrier, and the platinum/tin alloy is present at a single platinum/tin molar ratio within a range of a predetermined thickness from an outer periphery of the carrier,
   wherein the predetermined thickness from the outer periphery of the carrier is 300 to 500 μm thick.

2. The catalyst according to claim 1, wherein the alkali metal is selected from the group consisting of potassium, sodium, and lithium.

* * * * *